(12) United States Patent
Spurgeon et al.

(10) Patent No.: US 8,614,098 B2
(45) Date of Patent: Dec. 24, 2013

(54) URINE GENDER TEST

(75) Inventors: John Spurgeon, Whitesboro, TX (US); Constance M. Hendrickson, Irving, TX (US)

(73) Assignee: Hello Baby F.S.T., LLC, Whitesboro, TX (US)

( * ) Notice: Subject to any disclaimer, the term of this patent is extended or adjusted under 35 U.S.C. 154(b) by 1835 days.

(21) Appl. No.: 11/219,985

(22) Filed: Sep. 6, 2005

(65) Prior Publication Data

US 2006/0063270 A1    Mar. 23, 2006

Related U.S. Application Data

(60) Provisional application No. 60/612,411, filed on Sep. 23, 2004.

(51) Int. Cl.
*G01N 33/00*    (2006.01)

(52) U.S. Cl.
USPC .......................................... 436/166; 436/172

(58) Field of Classification Search
USPC ....................................... 422/50, 56, 68.1, 99
See application file for complete search history.

(56) References Cited

U.S. PATENT DOCUMENTS

| | | | |
|---|---|---|---|
| 4,840,914 A | | 6/1989 | Weisberg |
| 5,709,837 A | * | 1/1998 | Mori et al. ...................... 422/56 |
| 6,420,182 B1 | | 7/2002 | Start |

OTHER PUBLICATIONS

Ostler, et al.; "Fetal sex determination: the predictive value of 3 common myths"; JAMC, Dec. 14, 1999; pp. 1525-1526.

* cited by examiner

*Primary Examiner* — Sam P Siefke
(74) *Attorney, Agent, or Firm* — Edwin S. Flores; Chainey P. Singleton

(57) ABSTRACT

A solid composition for determining the gender of an unborn fetus, comprising a first layer comprising a basic salt, a second layer comprising a transition metal, and a third layer comprising a neutral filler separating the first and second layers.

20 Claims, 9 Drawing Sheets

URINE GENDER TEST

CROSS-REFERENCE TO RELATED APPLICATIONS

This application claims the benefit of U.S. Provisional Application 60/612,411 entitled, "URINE GENDER TEST," to John Spurgeon and Constance M. Hendrickson, filed on Sep. 23, 2004, which is incorporated by reference herein in its entirety.

TECHNICAL FIELD OF THE INVENTION

The present invention is directed, in general, to determining the gender of an unborn fetus by testing the urine from a pregnant mother, and more particularly, a composition, method and kit to facilitate such testing.

BACKGROUND OF THE INVENTION

There is great interest in determining the gender of an unborn fetus. For instances, parents are curious to know the sex of their unborn child. Knowledge of a fetus's gender would allow animal breeders to better manage various aspects of their business, including selling and purchase, insurance, mating decisions. Unfortunately, an accurate gender test that is both inexpensive and simple to perform is not available.

Various tests, such as the Draino test, while inexpensive and simple to perform, has been dismissed by the medical establishment as having no value for predicting fetal sex. Other techniques that are accepted as accurate, are either invasive, such as amniocentesis or maternal blood tests, or require expensive equipment, such as ultrasound or x-rays. Moreover, such techniques are not without dangers to the fetus and are not completely reliable.

Accordingly, what is needed in the art is a gender test that does not suffer from the disadvantages associated with conventional gender tests, as discussed above.

SUMMARY OF THE INVENTION

To address the above-discussed deficiencies of the prior art, the present invention provides in one embodiment, a solid composition for determining the gender of an unborn fetus. The composition comprises a first layer comprising a basic salt, and a second layer comprising a transition metal. The composition further includes a third layer comprising a neutral filler that separates the first and second layer.

The foregoing has outlined preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the scope of the invention.

BRIEF DESCRIPTION OF THE DRAWINGS

For a more complete understanding of the present invention, reference is now made to the following detailed description taken in conjunction with the accompanying FIGUREs. It is emphasized that various features may not be drawn to scale. In fact, the dimensions of various features may be arbitrarily increased or reduced for clarity of discussion. Reference is now made to the following descriptions taken in conjunction with the accompanying drawings, in which.

DETAILED DESCRIPTION

Figure 1:
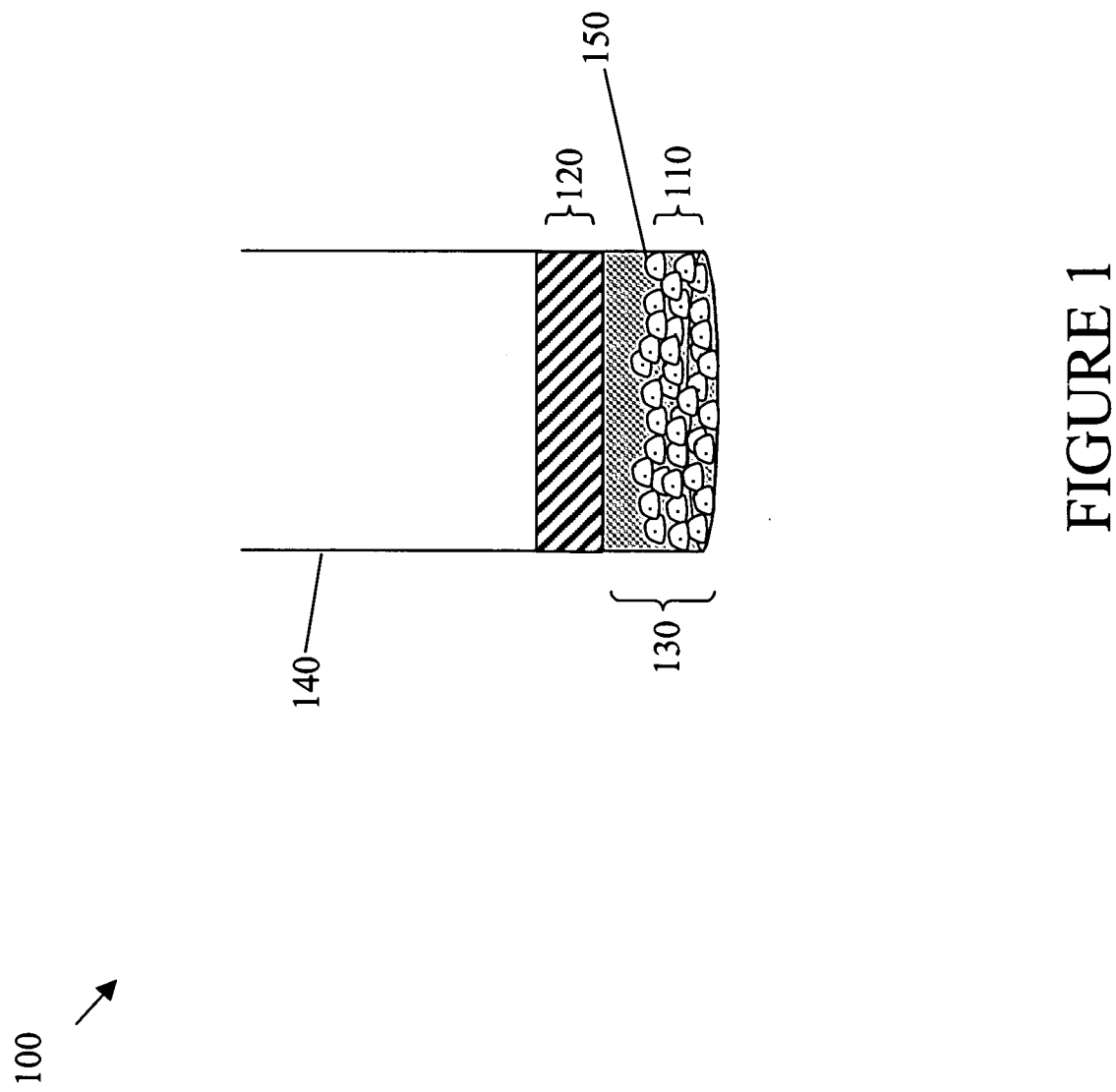
FIG. 1 illustrates a cross-sectional view of an exemplary solid composition of the present invention for gender testing.

One embodiment of the present invention is a solid composition for determining the gender of an unborn fetus. The term fetus, as used herein is defined as the unborn offspring of any animal species, such as human, bovine and equine species. FIG. 1 illustrates a cross-sectional view of an exemplary solid composition 100 of the present invention. The present invention benefits from the recognition that the shelf-life of the solid composition 100 can be advantageously extended by keeping certain components of the solid composition 100 separated, to prevent the undesired premature reaction of these components.

As illustrated in FIG. 1, the solid composition 100 comprises a first layer 110, a second layer 120 and a third layer 130. The third layer 130 separates the first layer 110 from the second layer 120. The first layer 110 comprises a basic salt. As well known to those of ordinary skill in the art, a basic salt is defined as a salt that contains more of the basic constituent than is required to neutralize the acid of the salt. In some preferred embodiments, the basic salt of the first layer 100 comprises a water-soluble alkali metal hydroxide. In some embodiments, the basic salt comprises lithium hydroxide (LiOH), sodium hydroxide (NaOH), potassium hydroxide (KOH) or a mixture thereof. In some cases, the basic salt preferably comprises a non-deliquescent basic salt, such as LiOH, because such salts are less prone to absorb water and carbon dioxide from air and thereby do not liquefy during storage as rapidly as deliquescent basic salts such as KOH or NaOH. The liquefaction of the first layer 110 can cause the undesirable premature mixing and reaction of the components of the first and second layers 110, 120. In some cases, the basic salt preferably comprises NaOH or KOH, because these salts generate a large amount of heat when it dissolves in water or urine. The generation of heat, in turn, facilitates other components to dissolve when the solid composition 100 is mixed with urine for gender testing.

In some advantageous embodiments, such as that shown in FIG. 1, the first layer 110, comprising a basic salt is a top layer of the solid composition 100 located in a container 140. In other preferred embodiments, however, the first layer 110 can be a bottom layer of the composition 100. Preferably, the first layer 110 comprises solid particles of the basic salt whose size is carefully selected. The selection balances the desire for the particle size to be small enough to rapidly dissolve in an aqueous solution, versus having a large enough size to retain the separation of the first and second layer 110, 120 via the third layer 130. In some instances, the first layer 110 comprises pellets or flakes having an average diameter ranging from about 1 millimeter to 10 millimeters. In some preferred embodiments, the first layer 110 comprises about 5 to about 25 percent of the total weight of the solid composition 100.

The second layer 120 comprises a transition metal. For the purposes of the present invention, a transition metal is defined as any element in Periods 4-6 and Groups 3-12 of the Periodic Table of Elements (International Union of Pure and Applied Chemist Convention for designating Groups and Periods). In some preferred embodiments, the transition metal, upon being dissolved in an aqueous solution, forms ions having a valance of +2 or +3. In some embodiments of the solid composition 100, the transition metal comprises aluminum, iron or a mixture thereof. In certain preferred embodiments, the transition metal comprises aluminum because aluminum is less prone to oxidation than iron when the solid composition 100 is stored over a period of 3 to 4 months. In addition, the solid composition 100 comprising aluminum provides a more readily recognizable color difference between positive and negative results in gender tests, as compared to an iron-containing solid composition 100.

In certain preferred embodiments, such as shown in FIG. 1, the second layer 120 is a bottom layer of the solid composition 100 in the container 140. In other preferred embodiments, however, the second layer 120 can be the top layer of the solid composition 100. Preferably, the second layer 120 comprises solid particles 150 of the transition metal whose size and amount is carefully selected. The selected size and amount of transition metal balances the desire for the particle size to be small enough to rapidly dissolve and react with the basic salt and urine sample but not to have an excessively violent reaction. An excessively violent reaction might result in the frothing of the solid composition 100 or the urine sample out of the container 140 or cause the container 140 to explode.

In some instances, the second layer 120 advantageously comprises particles 150, such as shot or filings, having an average diameter ranging from about 1 millimeter to 2 millimeters. In some preferred embodiments, the second layer 110 comprises about 4 to about 20 percent, and more preferably about 4 to about 12 percent, of the total weight of the solid composition 100.

The third layer 130 comprises a neutral filler. The neutral filler can comprise a neutral salt, a water soluable polymer, or both, and is configured to separate the first and second layers 110, 120. Keeping the basic salt of the first layer 110 and transition metal of the second layer 120 separated advantageously extends the shelf life of the solid composition 100. The shelf life is extended by deterring oxidation and other reactions between the basic salt and the transition metal of the first and second layers, 110, 120, respectively. For example, embodiments of the solid composition 100 of the present invention can be kept for periods of up to about 4 months and then successfully used for gender testing. This is in contrast to formulations comprising a basic salt and a transition metal in intimate contact with each other. In such formulations, the basic salt and transition metal start reacting with each other within minutes of their preparation.

As well known to those of ordinary skill in the art, a neutral salt is formed by the complete replacement of the hydrogen in an acid or base, in the former case by a positive or basic element or radical, in the latter case by a negative or acidic element or radical. Preferred embodiments of the neutral salt comprises a water soluable salt such as alkali halides, sulfates or nitrates. Preferred embodiments of the neutral filler comprising the water soluable polymer include polyvinyl alcohol.

In certain advantageous embodiments, such as shown in FIG. 1, the third layer 130 is located between the first and second layers 110, 120. More preferably, as also shown in FIG. 1, the third layer 130 encapsulates the particles of second layer 120. In other preferred embodiments, however, the third layer 130 can encapsulate the basic salt of the first layer 110. In some preferred embodiments, the third layer 130 comprises about 30 to about 80 percent, and more preferably about 55 to about 80 percent, of the total weight of the solid composition 100.

In still other preferred embodiments the solid composition 100 further includes an indicator. The indicator advantageously facilitates a more prominent color change in the solution resulting from mixing the solid composition 100 with testosterone-containing urine as compared to testosterone-free urine during gender testing. The indicator can comprise any acid-base indicator that preferably turns pink or red with high pH. In some preferred embodiments, the indicator 160 comprises alizarin, alizarin yellow R, o-cresolphthalein, cresol red, phenol red, phenolphalien, or mixtures thereof. In certain advantageous cases, such as shown in FIG. 1, the third layer 130 includes the indicator. In other cases, not illustrated, the first layer includes the indicator, and in still other instances, both the first and third layer includes the indicator. In some preferred embodiments, the indicator comprises about 0.1 to about 0.3 percent of the total weight of the solid composition 100.

Another aspect of the present invention is a method for preparing a solid composition for determining the gender of an unborn fetus. FIGS. 2 to 5 illustrate cross-sectional views of selected steps in an exemplary method of preparing a solid composition 200 according to the principles of the present invention. Any embodiments of the solid composition, and its the components discussed above and illustrated in FIG. 1, can be made according to the method.

Figure 2:
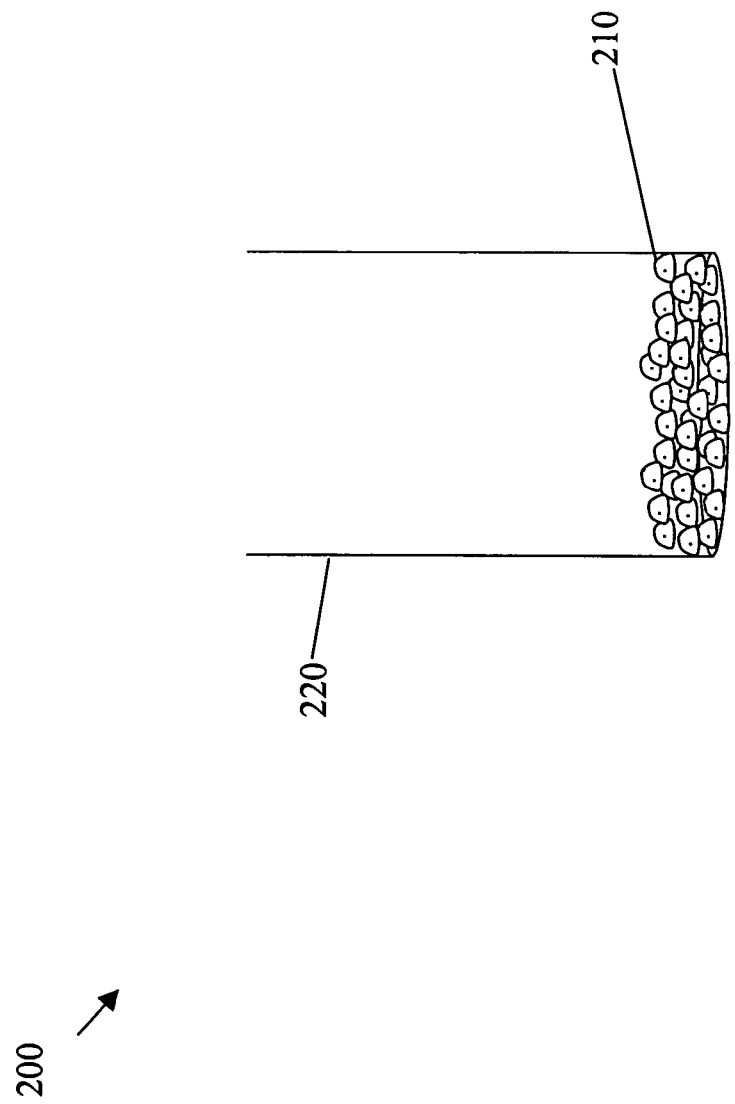
FIGS. 2-6 illustrate cross-sectional views of selected steps in an exemplary method of manufacturing a solid composition for gender testing according to the principles of the present invention.

Turning first to FIG. 2, illustrated is the partially completed solid composition 200, after a placing a transition metal 210 in a container 220.

Figure 3:
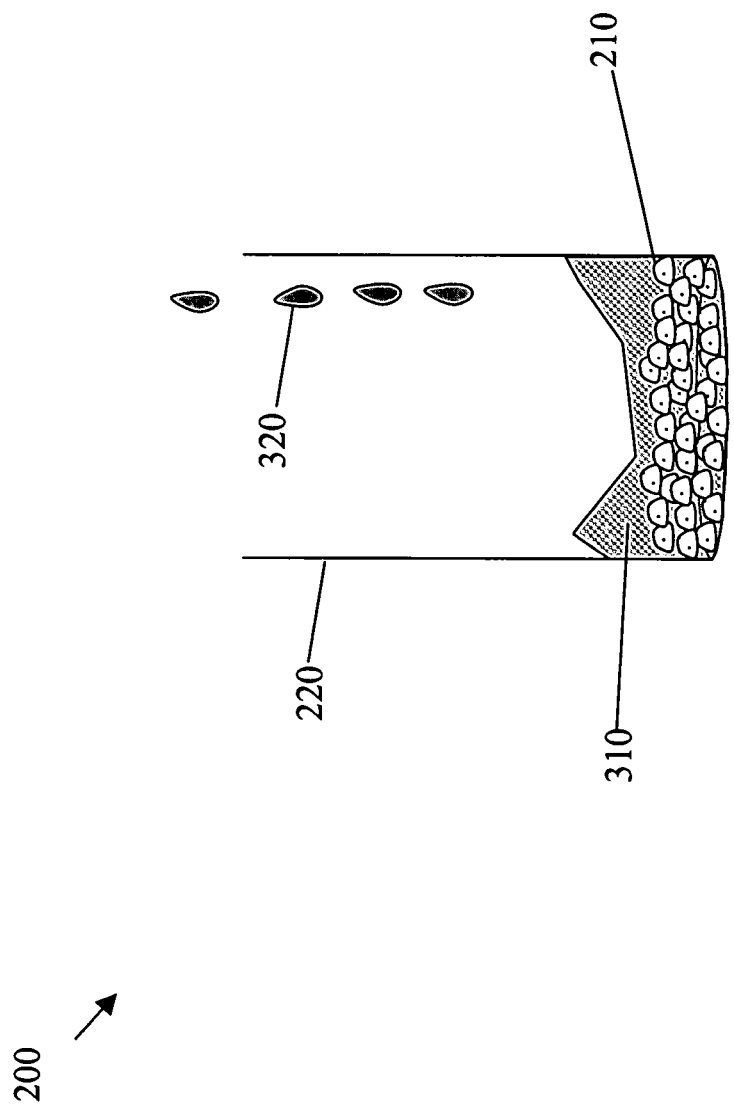
Figure 4:
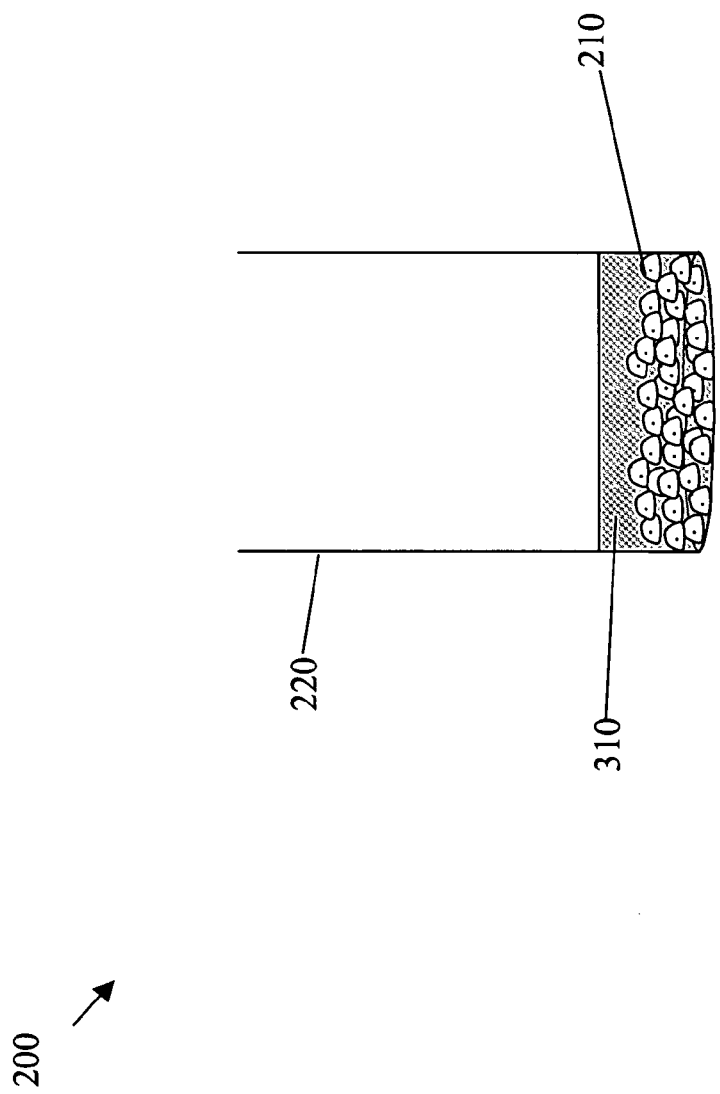

FIGS. 3 and 4 illustrate placing a neutral filler 310 in the container 220. In the illustrated embodiment, the filler 310 covers the transition metal 210. More preferably, the filler 310 encapsulates the transition metal 210. Turning first to FIG. 3, to facilitate encapsulation of the transition metal 210 by the neutral filler 310, a liquid 320 is added to wash the transition metal 210 and the neutral filler 310 to the bottom of the container 220.

In some cases, the neutral filler 310 comprises a neutral salt dissolved in the liquid 320 to form a solution, and the solution is placed in the container 220. In some instances, the liquid 320 comprises water, a volatile organic solvent such as acetone or ethanol, or a mixture thereof. In still other cases, the neutral salt 310, the liquid 320, or both, or a solution thereof, are placed in the container 220, and then the transition metal 210 is added to the container 220. In other embodiments, the neutral filler 310 comprises a water soluable organic polymer.

With continuing reference to FIG. 3, FIG. 4 shows the partially completed solid composition 200 after drying to leave the transition metal 210 encapsulated and covered by the neutral filler 310. Drying can be accomplished by heating to slightly below the boiling point of the liquid 320 (e.g., about 94° C. when the liquid is water). Alternatively, drying can be achieved in vacuum at room temperature (about 20° C.) or at lower than room temperatures, via freeze-drying. In some cases, as illustrated in FIG. 4, drying removes the liquid 320 thereby allowing the neutral salt of the neutral filler 310 to precipitate and crystallize around the transition metal 210. In other cases, drying condenses the water soluable organic polymer of the neutral filler 310, so that the organic polymer surrounds the transition metal 210.

Figure 5:
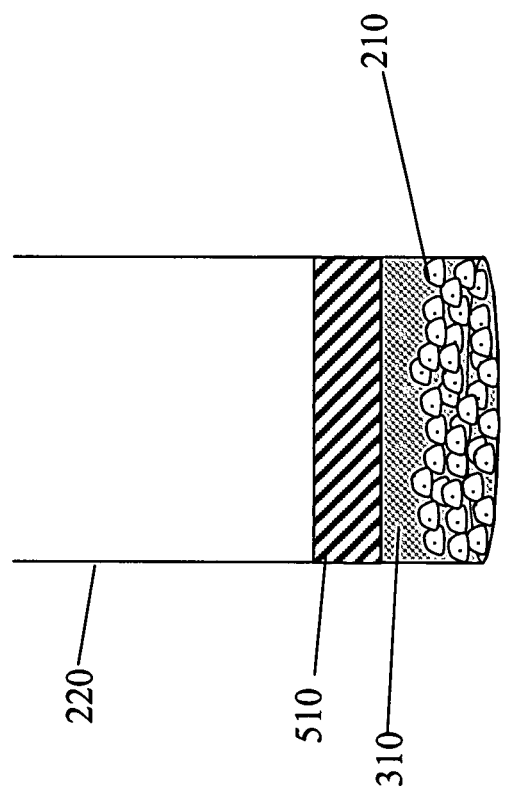

Turning now to FIG. 5, illustrated is the partially completed solid composition 200, after adding a basic salt 510 to the container 220. In some preferred embodiments, as illustrated in FIG. 5, the basic salt 510 is placed over the neutral filler 310. The neutral filler 310 thereby separates the transition metal 210 and the basic salt 510.

Though not illustrated, in other embodiments of the method, an optional indicator such as described above, is added to one or both of the neutral filler 310 or the basic salt 510. In alternative embodiments of the method, the basic salt 510 is placed in the container first, followed by adding the neutral filler 310, to cover the basic salt, and then adding the transition metal 210. In yet other cases, the neutral filler 310 and basic salt 510, and optional indicator, are mixed together, and then moistened with a liquid 320 to facilitate their placement in the bottom of the container 220, followed by drying, and then the transition metal 210 is placed over the neutral filler 310.

Figure 6:
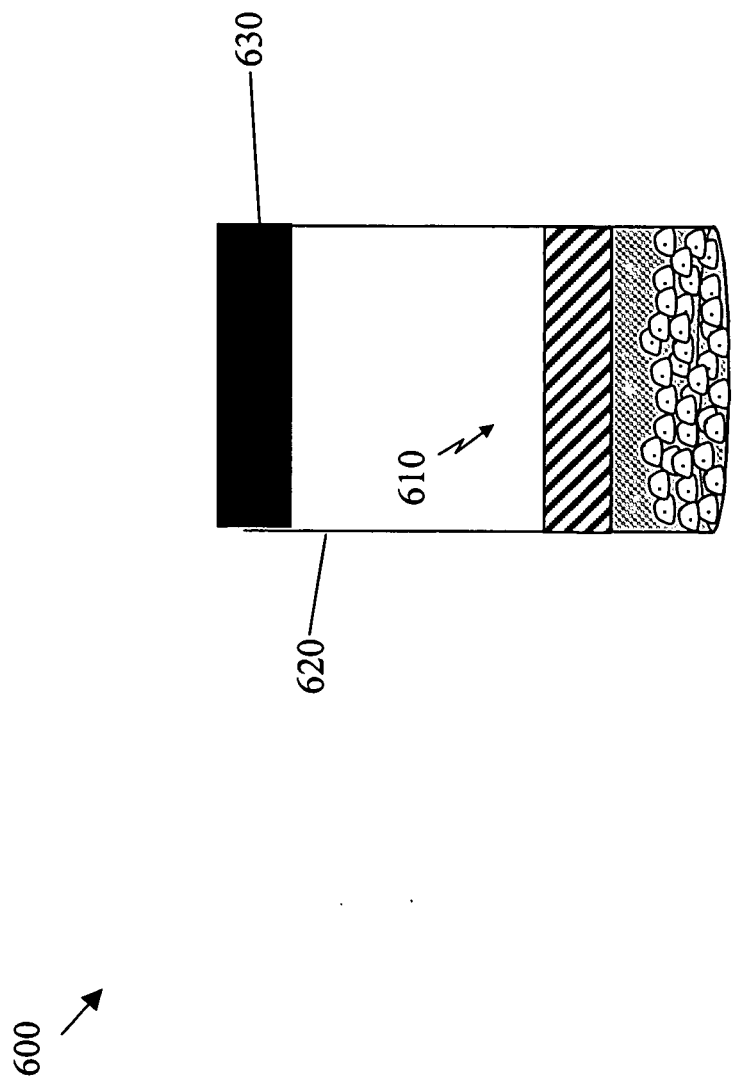

Yet another aspect of the present invention is a kit for determining the gender of an unborn fetus. FIG. 6 illustrates a cross-sectional view of an exemplary kit 600 of the present invention. The kit 600 comprises a solid composition 610 located in a reaction vessel 620. Any of the embodiments of the solid composition discussed above and illustrated in FIGS. 1-5 can be included in the kit 600. Some preferred embodiments of the reaction vessel 620 comprise a non-metallic material, and more preferably, the reaction vessel 620 is substantially non-reactive with the components of the solid composition 610. Preferred embodiments of the reaction vessel 620 comprise glass or plastic tubes or vials.

The solid composition 600 is separated from the ambient environment surrounding the reaction vessel 620 by a seal 630 covering an opening in the reaction vessel 620. The seal 630 advantageously deters the uptake of moisture from the ambient environment into the solid composition 610. If it absorbs sufficient quantities of moisture, components of the solid composition 610 can get mixed together and react as discussed above, thereby spoiling the kit 600.

In some preferred embodiments, the seal 630 comprises a wax that forms an airtight closure over an opening in the reaction vessel. Preferred waxes comprise a petroleum wax such as paraffin wax, although other animal, plant or synthetic waxes can be used. In other embodiments, however, the seal comprises a plastic screw top cap or similar airtight closure. Alternatively, the top of the reaction vessel 620 can be sealed by melting the upper portion of the reaction vessel 620 together.

Forming an airtight seal 630 over the reaction vessel 620 advantageously extends the shelf life of the kit 600. For example, in some embodiments of the kit 600 having a seal 630 made of paraffin wax, the kit 600 can be stored for least about 2 years before being successfully used. In comparison, similarly formulated solid compositions 610 placed in unsealed reaction vessels 620 have a shelf-life up to about 4 months.

Figure 7:
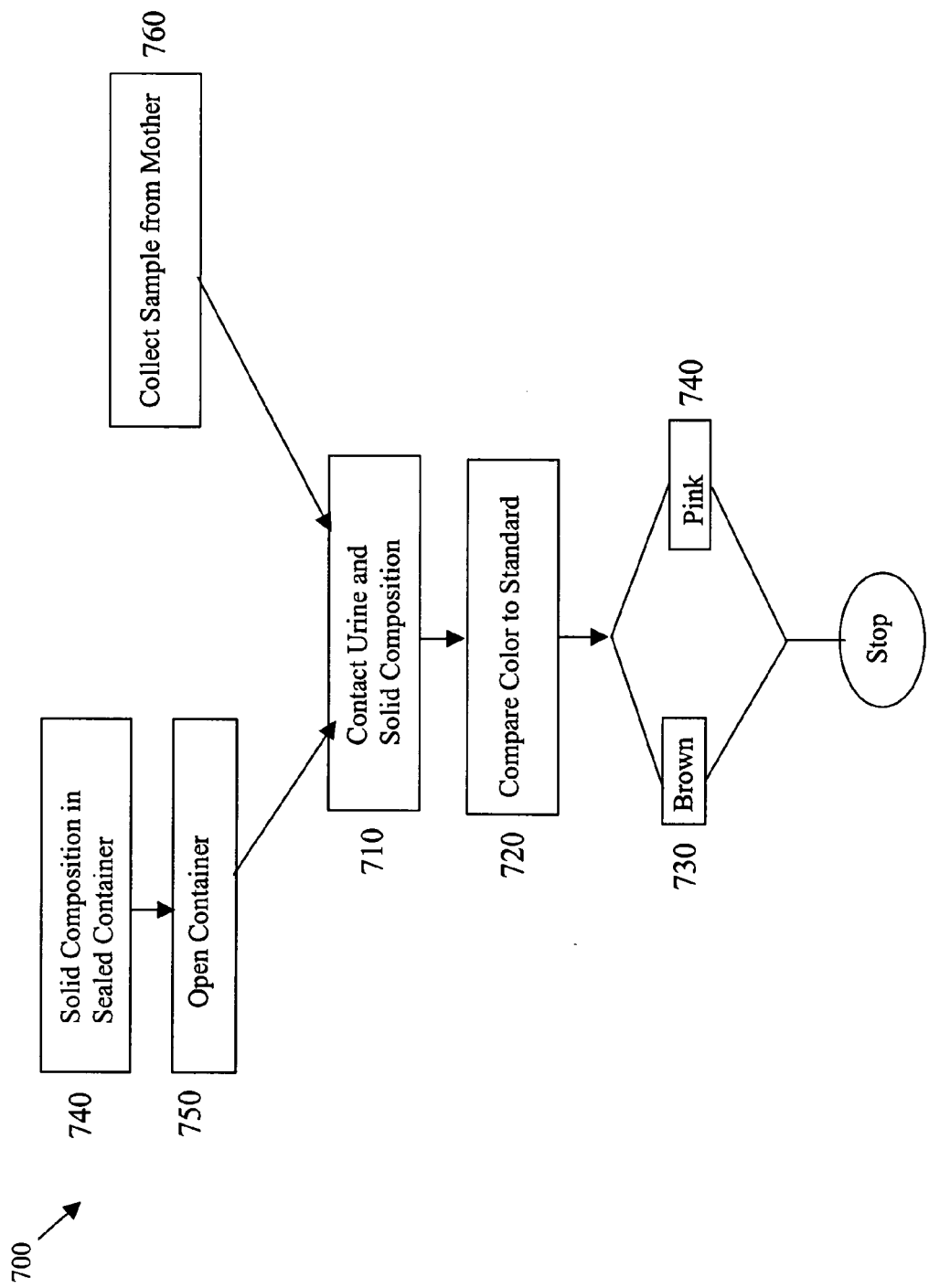
FIG. 7 illustrates by flow diagram, an exemplary method of determining the gender of an unborn fetus according to the principles of the present invention.

Still another aspect of the present invention is a method of determining the gender of an unborn fetus. FIG. 7 illustrates by flow diagram an exemplary method 700 of determining the gender of an unborn fetus according to the principles of the present invention. The method 700 comprises in step 710, contacting urine from a mother of the unborn fetus with a solid composition of the present invention to form a solution. Any of the embodiments of the solid composition and its packaging discussed herein can be used in the method 700. The method 700 further includes in step 720, comparing a color of the solution to a color standard to determine a gender of the unborn fetus.

FIG. 7, further illustrates aspects of the color comparison. In step 730, the solution turns dark brown when the urine is from a mother pregnant with a male fetus. As illustrated in step 740, in some preferred embodiments, when the urine from a mother pregnant with a female fetus is added to the solid composition that includes an indicator, the resulting solution turns pink or red.

As exemplified in step 740, in some preferred embodiments, the solid composition is stored in a sealed container. Then, as shown in step 750, shortly before testing, the seal of the container is opened so that urine from the mother can be added to the container. In some preferred embodiments, the seal is opened within about 1 hour of adding urine to the container. As further exemplified by step 760, the urine sample is preferably obtained from the mother within about 1 hour before adding the urine to the container holding the solid composition.

Having described the present invention, it is believed that the same will become even more apparent by reference to the following examples. It will be appreciated that the examples are presented solely for the purpose of illustration and should not be construed as limiting the invention. For instance, although the studies described below may be carried out in a laboratory setting, one skilled in the art could adjust specific numbers, dimensions and quantities up to appropriate values for a full-scale plant setting.

EXAMPLES

Exemplary data collected as part of the present invention is depicted below to: 1) illustrate the preparation of various solid compositions of the present invention; 2) demonstrate the superior stability of the solid composition of the present invention as compared to a prior art formulation; 3) present test results to demonstrate the determination of gender in humans using test kits of the present invention; and 4) present test results to illustrate the feasibility of determining gender in bovine and equine species.

Various solid compositions were prepared and subject to stability testing and to investigate gender testing. One solid composition (designated SC-1) comprised a transition metal of iron powder, a neutral filler of KCl, and a basic salt of KOH, in weight percentages of 10%, 65%, and 25%, respectively. A second solid composition (designated SC-2) comprised a transition metal of aluminum powder, a neutral filler of sodium nitrate ($NaNO_3$) and a basic salt of NaOH in weight percentages of 5%, 75%, and 20%, respectively. A third solid composition (designated SC-3) comprised a transition metal of aluminum shot (average diameter of between about 1 and 2 mm), a neutral filler of NaCl and $NaNO_3$, and a basic salt of NaOH in weight percentages of 6%, 20%, 60%, and 14%, respectively. A fourth solid composition (designated SC-4) comprised a transition metal of iron filings, a neutral filler of potassium chloride (KCl) and potassium nitrate ($KNO_3$) and a basic salt of NaOH in weight percentages of 12%, 25%, 55%, and 6%, respectively.

In one study, a solid composition (designated SC-5) used for stability testing was composed of the same transition metal, neutral filler and basic salt, and substantially the same proportions thereof, as SC-3. The aluminum shot was added to a glass test tube and then a neutral filler comprising NaCl and $NaNO_3$ (about 1:3 weight ratio) was added to the test tube. In addition, an indicator of about 0.1 weight percent phenolphthalein was added to the test tube. Next, several drops of water were added to the tube to wet the neutral filler, indicator and aluminum shot. The test tube was then gently tapped to ensure that all of the aluminum shot was at the bottom of the test tube and covered by the wet neutral filler. The tube was then heated to about 94° C. to evaporate the water. As the water evaporated, the neutral filler crystallized, thereby encapsulating the transition metal underneath the neutral filler. After cooling the tube, the NaOH pellets were added to the tube over the neutral filler. In some preparations, the tube was then sealed with paraffin wax until used for testing, while in other preparations the tube was left exposed to the ambient environment (about 50 to 85 percent relative humidity).

Figure 8A:
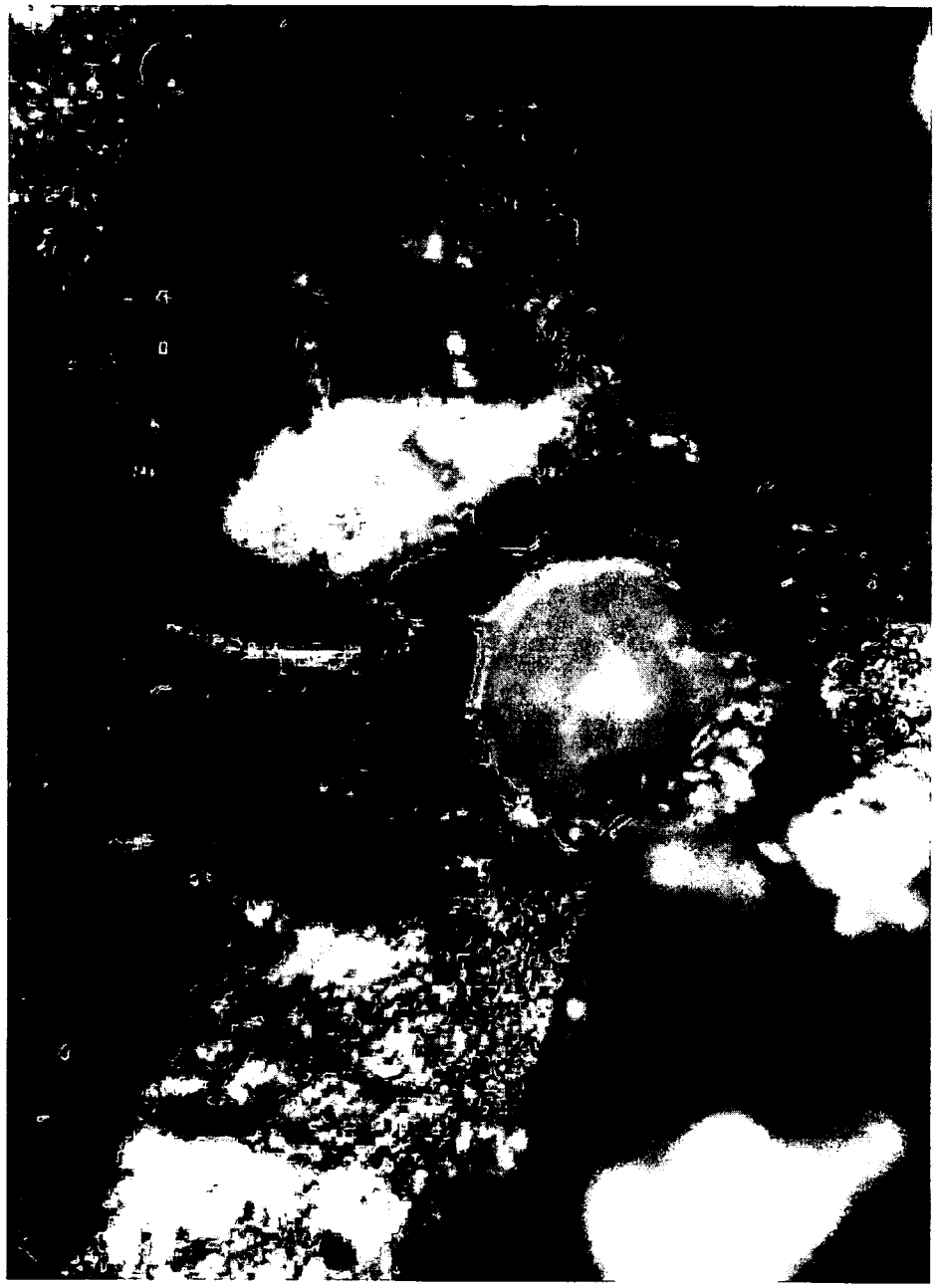
FIGS. 8A and 8B present representative microphotographs of a typical prior art composition, at two different magnifications, minutes after mixing components of the composition.
Figure 8B:
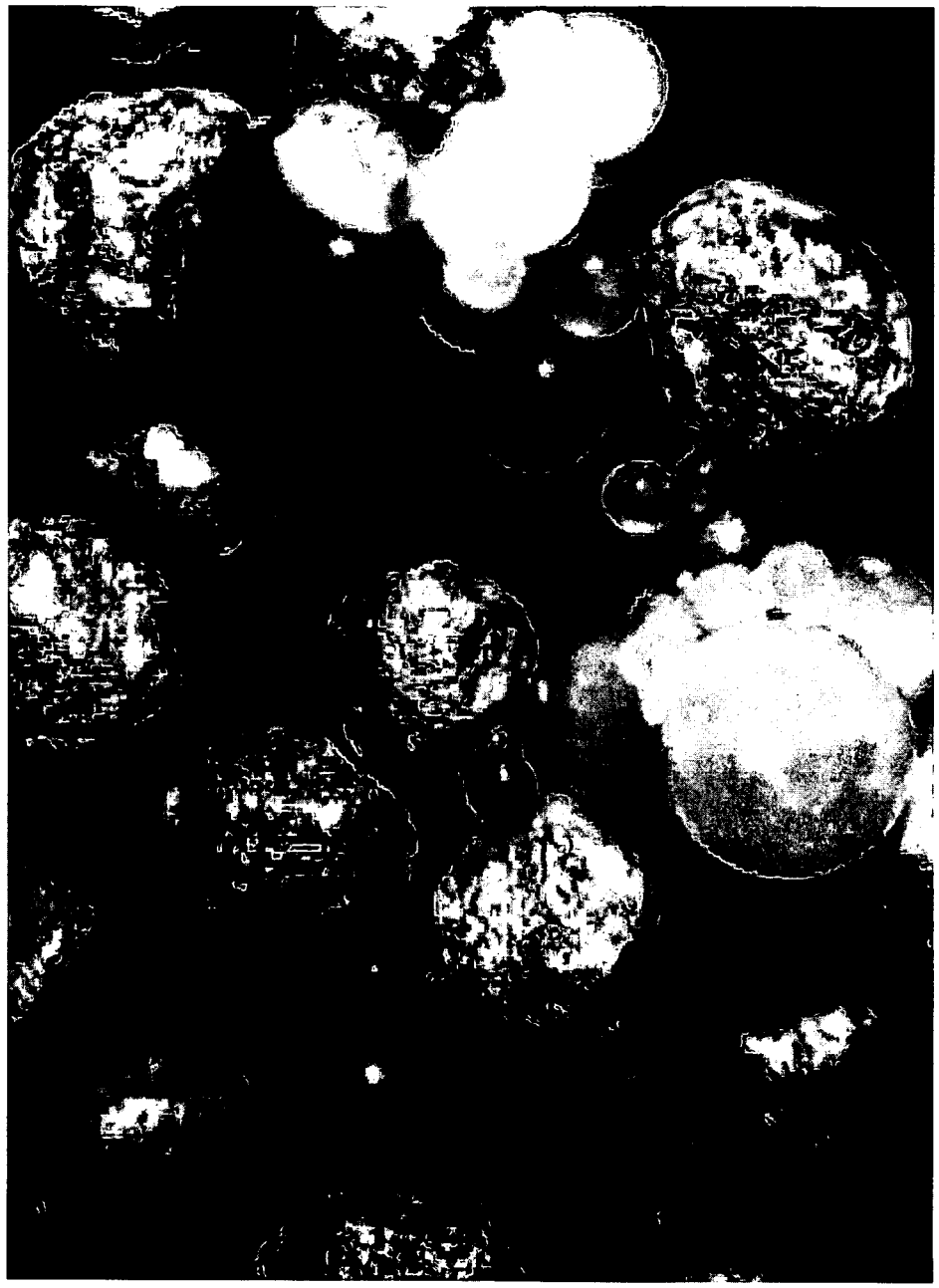

For comparative purposes, a test formulation (designated F-1) was prepared by mixing the aluminum shot with NaOH in proportions of 50:50 (wt/wt), with no neutral filler present in the formulation. Preparation F-1 is representative of prior art formulation where aluminum and alkali hydroxide are in intimate contact with each other. FIGS. 8A and 8B presents representative microphotographs, at two different magnifications, of the F-1 preparation minutes (e.g., less than 10 minutes) after mixing the aluminum shot and NaOH together. Substantial oxidation reactions between the aluminum shot and NaOH were observed, the reaction continuing until either all the aluminum or the NaOH was consumed. Similar experiments where similar proportions of aluminum powder and NaOH were mixed directly together resulted in a violent reaction, and in some cases, explosion of the reaction vessel.

Additional experiments were performed to evaluate the long-term stability of the SC-5 preparation. Several test tubes containing the SC-5 preparation were stored in unsealed test tubes. These preparations worked accurately for gender testing for up to about 3.5 months. Thereafter, the accumulation of moisture in the test tubes became visible. The content of all of the tubes had undergone substantial reactions after about 4.25 months. Dramatically longer stabilities were observed for several test tubes containing SC-5 preparations in sealed test tubes. Preparations of SC-5 stored in sealed tubes have been accurately used for gender test after about 24 months of storage. Similar stabilities have been obtained for preparations stored in containers with damp tight packages.

Representative results for gender test performed using the SC-5 preparation on human subject are shown in Table 1. Similar test results for equine and bovine subjects are shown in TABLE 2.

TABLE 1

| Sample Number | Mother's Age (Years) | Gestational Age at Testing (Weeks) | Test Result | Confirmed Result |
|---|---|---|---|---|
| 1 | 19 | 16.5 WKS | F | F |
| 2 | 38 | 26 WKS | F | F |
| 3 | 15 | 19 WKS | M | M |
| 4 | 20 | 17 WKS | F | F |
| 5 | 19 | 16 WKS | M | F |
| TWINS DIFFERENT GENDER | | | | |
| 6 | 21 | 21 WKS | F | F |
| 7 | 31 | 18 WKS | F | M |
| TWINS DIFFERENT GENDER | | | | |
| 8 | 36 | 18 WKS | F | F |
| 9 | 18 | 19 WKS | F | F |
| 10 | 23 | 17 WKS | M | M |
| 11 | 28 | 19 WKS | M | M |
| 12 | 22 | 20 WKS | F | F |
| 13 | 23 | 21 WKS | F | F |
| 14 | 21 | 20 WKS | F | F |
| 15 | 19 | 22 WKS | M | M |
| 16 | 26 | 16 WKS | M | M |
| 17 | 25 | 15.5 WKS | F | F |
| 18 | 22 | 18 WKS | F | F |
| 19 | 31 | 19.5 WKS | F | F |
| 20 | 18 | 16 WKS | F | M |
| EVENING URINE | | | | |
| 21 | 19 | 17 WKS | M | M |
| 22 | 20 | 21 WKS | F | F |
| 23 | 20 | 20 WKS | F | F |
| 24 | 26 | 22 WKS | F | F |
| 24 | 20 | 20 WKS | F | F |
| 25 | 22 | 21 WKS | M | M |
| 26 | 22 | 16 WKS | F | F |
| 27 | 24 | 18 WKS | M | M |
| 28 | 24 | 19 WKS | M | M |
| 29 | 34 | 19 WKS | M | M |
| 30 | 39 | 14 WKS | F | M |
| TO EARLY IN GEST | | | | |
| 31 | 26 | 21 WKS | F | F |
| 32 | 28 | 20 WKS | F | F |
| 33 | 29 | 20 WKS | F | F |
| 34 | 31 | 22 WKS | F | F |
| 35 | 36 | 21 WKS | F | F |
| 36 | 27 | 17 WKS | F | F |
| 37 | 29 | 17 WKS | F | F |
| 38 | 24 | 19 WKS | F | F |
| 39 | 22 | 17 WKS | M | M |
| 40 | 26 | 17 WKS | M | M |
| 41 | 19 | 22.5 WKS | M | M |
| 42 | 21 | 21 WKS | F | F |
| 43 | 27 | 16 WKS | M | M |
| 44 | 25 | 17 WKS | F | F |
| 45 | 24 | 18 WKS | F | F |
| 46 | 31 | 21 WKS | F | F |
| 47 | 33 | 20 WKS | F | F |
| 48 | 23 | 20 WKS | F | F |
| 49 | 19 | 19 WKS | F | F |
| 50 | 28 | 21 WKS | M | M |
| 51 | 23 | 17 WKS | M | M |
| 52 | 20 | 16 WKS | F | |
| PREGNANCY MISCARRIED | | | | |
| 53 | 22 | 18 WKS | F | F |
| 54 | 28 | 18 WKS | M | M |
| 55 | 22 | 19 WKS | F | F |
| 56 | 21 | 20 WKS | F | F |
| 57 | 26 | 21 WKS | F | F |
| 58 | 24 | 16 WKS | F | F |
| 59 | 17 | 18 WKS | F | F |
| 60 | 19 | 17 WKS | F | F |
| 61 | 28 | 19 WKS | M | M |
| 62 | 23 | 17 WKS | M | M |
| 63 | 22 | 19 WKS | M | M |
| 64 | 21 | 19 WKS | F | F |
| 65 | 24 | 22 WKS | F | F |
| TWINS | | | | |
| 66 | 35 | 18 WKS | F | F |
| 67 | 31 | 19 WKS | F | F |
| 68 | 39 | 17 WKS | F | F |
| 69 | 43 | 17 WKS | M | M |
| 70 | 17 | 21 WKS | M | M |
| 71 | 18 | 22 WKS | F | F |
| 72 | 19 | 16 WKS | M | F |
| NOT SUPERVISED TEST | | | | |
| 73 | 23 | 18 WKS | F | F |
| 74 | 26 | 17 WKS | F | F |
| 75 | 25 | 16 WKS | M | M |
| 76 | 21 | 18.5 WKS | F | F |
| 77 | 17 | 20 WKS | M | M |
| 78 | 23 | 21 WKS | M | M |
| 79 | 19 | 24 WKS | F | F |
| 80 | 27 | 22 WKS | M | M |
| 81 | 22 | 19 WKS | F | F |

TABLE 1-continued

| Sample Number | Mother's Age (Years) | Gestational Age at Testing (Weeks) | Test Result | Confirmed Result |
|---|---|---|---|---|
| 82 | 27 | 19 WKS | F | F |
| 83 | 33 | 17 WKS | F | F |
| 84 | 29 | 18 WKS | F | F |
| 85 | 20 | 18 WKS | F | F |
| 86 | 20 | 19 WKS | F | F |
| 87 | 24 | 19 WKS | M | M |
| 88 | 19 | 21 WKS | M | M |
| 89 | 18 | 22 WKS | F | F |
| 90 | 38 | 20 WKS | F | F |
| 91 | UNKNOWN | 22 WKS | F | F |
| 92 | 24 | 21 WKS | M | M |
| 93 | 19 | 22 WKS | F | F |
| 94 | 22 | 19 WKS | F | F |
| 95 | 26 | 17 WKS | M | M |

TABLE 2

| Species | Mother's Age (Years) | Gestational Age at Testing (Weeks) | Test Result | Confirmed Result |
|---|---|---|---|---|
| Equine | 8 | 20 | M | M |
| Bovine 1 | 17 | 18 | F | F |
| Bovine 2 | 9 | 22 | F | F |

Although the present invention has been described in detail, those skilled in the art should understand that they can make various changes, substitutions and alterations herein without departing from the scope of the invention in its broadest form.

What is claimed is:

1. A gender testing device comprising a solid composition for determining the gender of an unborn fetus, the composition comprising:
    a first layer comprising a basic salt;
    a second layer comprising a transition metal; and
    a third layer comprising a neutral filler separating said first layer and said second layer.

2. The composition as recited in claim 1, wherein said basic salt comprises a water-soluble alkali metal hydroxide.

3. The composition as recited in claim 1, wherein said basic salt comprises sodium hydroxide.

4. The composition as recited in claim 1, wherein said basic salt comprises potassium hydroxide.

5. The composition as recited in claim 1, wherein said basic salt comprises lithium hydroxide.

6. The composition as recited in claim 1, wherein said basic salt comprises particles having an average diameter ranging from about 1 millimeter to 10 millimeters.

7. The composition as recited in claim 1, wherein said transition metal comprises aluminum.

8. The composition as recited in claim 1, wherein said transition metal comprises particles having an average diameter ranging from about 1 millimeter to 2 millimeters.

9. The composition as recited in claim 1, wherein said neutral filler comprises a neutral salt.

10. The composition as recited in claim 1, wherein said neutral filler comprises a water-soluble polymer.

11. The composition as recited in claim 1, further comprising an indicator configured to enhance a color change in a solution resulting from mixing said solid composition with testosterone-containing urine.

12. The composition as recited in claim 1, wherein said first layer is a bottom layer of said solid composition.

13. The composition as recited in claim 1, wherein said first, said second and said third layer comprise portions of a kit for determining the gender of an unborn born fetus, said kit comprising:
    said solid composition recited in claim 1 located in a reaction vessel; and
    said solid composition is separated from ambient environment surrounding said reaction vessel by a seal covering an opening in said reaction vessel.

14. The composition as recited in claim 13, wherein said seal comprises a wax that forms an airtight closure over an opening in said reaction vessel.

15. A method for determining the gender of an unborn fetus, comprising:
    contacting urine from a mother of said unborn fetus with said solid composition recited in claim 1 to form a solution; and
    comparing a color of said solution to a color standard to determine a gender of said unborn fetus.

16. A method for preparing the solid composition as recited in claim 1, comprising:
    placing said transition metal in a container;
    adding said neutral filler to said container; and
    adding said basic salt to said container, wherein said neutral filler separates said transition metal and said basic salt.

17. The method as recited in claim 16, wherein adding said neutral filler comprises covering said transition metal with said filler.

18. The method as recited in claim 16, wherein adding said neutral filler comprises encapsulating said transition metal with said filler.

19. The method as recited in claim 18, wherein said encapsulating comprises adding a solution of said neutral filler dissolved in a liquid to said container and drying to remove said liquid.

20. The method as recited in claim 16, wherein adding said neutral filler comprises covering said basic salt.

* * * * *